United States Patent [19]

Burger et al.

[11] Patent Number: 4,751,079

[45] Date of Patent: Jun. 14, 1988

[54] INFECTIOUS BRONCHITIS VACCINES

[75] Inventors: Alois G. Burger, Doorn; Frans G. Davelaar, Putten; Heinrich D. Lütticken, Boxmeer, all of Netherlands

[73] Assignee: AKZO N.V., Arnhem, Netherlands

[21] Appl. No.: 462,221

[22] Filed: Jan. 31, 1983

[30] Foreign Application Priority Data

Feb. 5, 1982 [GB] United Kingdom ............... 8203400

[51] Int. Cl.[4] ..................... A61K 39/12; C12N 7/00; C12N 7/04
[52] U.S. Cl. ..................................... 424/89; 435/235; 435/236
[58] Field of Search .................... 435/235, 236; 424/89

[56] References Cited

U.S. PATENT DOCUMENTS 3,060,094 10/1962 Dutcher ............................... 435/235
3,876,763 4/1975 Yosnikazu et al. ................... 424/89
4,357,320 11/1982 Aponotweil et al. ................. 424/89

OTHER PUBLICATIONS

Bingham et al., J. Gen. Virol., 28:381-390 (1975).
Johnson et al., Avian Diseases, 20:173-178 (1976).
Raggi et al., Avian Diseases, 19:323-333 (1975).
Cowen et al., Avian Diseases, 19:583-595 (1975).
Alexander et al., Avian Pathology 5, 125-134, 1976.
M. S. Hofstad (Editor), *Diseases of Poultry*, 8th Ed., Iowa St. University Press, 1984, pp. 429-430.
Rose et al. (Editors), *Avian Immunology*, Edinburgh, British Poultry Science Ltd., 1981, pp. 205-226.
Darbyshire et al., Arch. Virol. 61, 227-238, 1979.
Winterfield et al., Avian Diseases, vol. 20, No. 1, pp. 42-48.
Davis et al., *Microbiology*, 2nd Edition, pp. 1034-1035.

*Primary Examiner*—Robert J. Warden
*Assistant Examiner*—Shawn P. Foley
*Attorney, Agent, or Firm*—Abelman Frayne Rezac & Schwab

[57] ABSTRACT

The present invention concerns infectious bronchitis vaccines derived from infectious bronchitis viruses which spontaneously hemagglutinate chicken erythrocytes, and processes for the preparation thereof, novel infectious bronchitis virus strains which spontaneously hemagglutinate chicken erythrocytes, and a method for immunization of egg-laying birds against infectious bronchitis.

33 Claims, 2 Drawing Sheets

FIG. 1 Distribution of HI Antibody Titers against Three IB Serotypes after vaccination with live D-274 Vaccine.
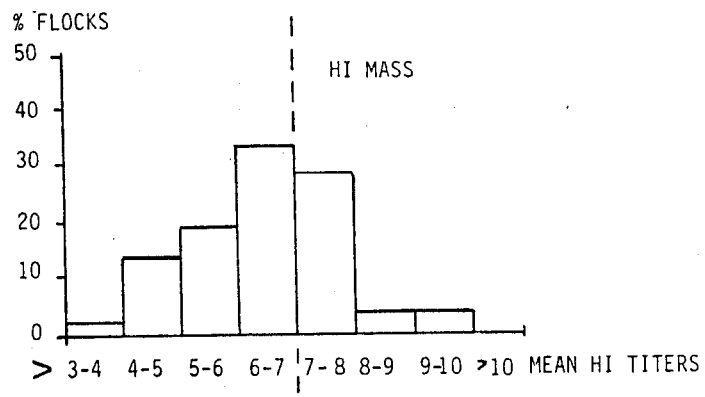
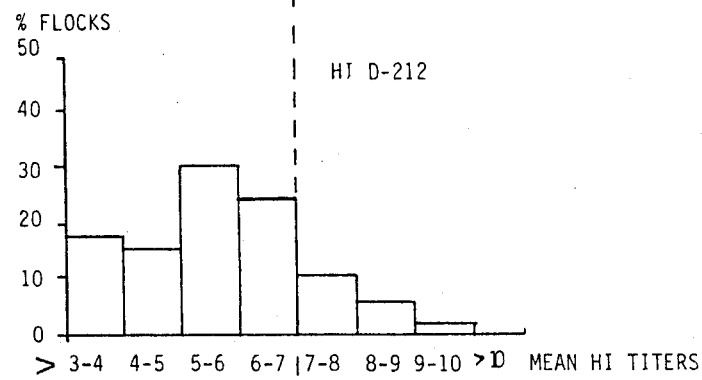
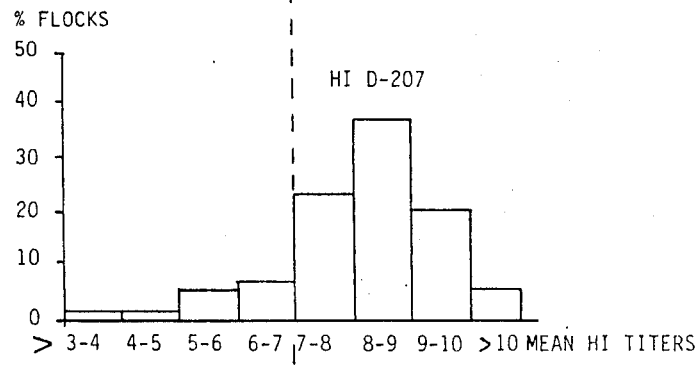

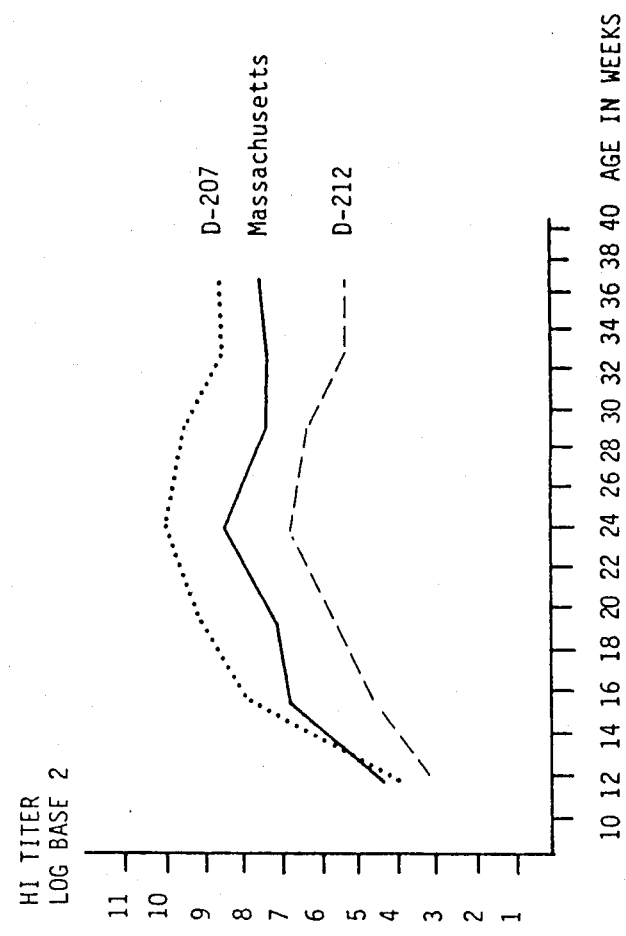
FIG. 2 Longitudinal survey of HI Titers of 16 flocks vaccinated at 1 day old with H120, at 16 weeks of age with H52 (Both Massachusetts type) and at 12 weeks of age with D274.

INFECTIOUS BRONCHITIS VACCINES

The invention is concerned with novel infectious bronchitis vaccines, a process for the preparation of live or inactivated infectious bronchitis vaccines, a method of immunization against Infectious Bronchitis and novel infectious bronchitis virus strains.

An avian corona virus is known to be the causative agent of an acute highly contagious respiratory disease in young and adult chickens characterized by tracheal rale, coughing, sneezing and nasal discharge. The disease, called Infectious Bronchitis (IB), can cause high mortality, particularly in young chickens and moreover kidneys and reproductive tract may be affected, the latter damage can result in a drop in egg production in layer respectively breeder hens. In many cases the egg drop is accompanied by an enteritis causing diarrhoea.

The chicken was considered to be the only natural host of the IB virus (IBV), but recently the virus has also been isolated from turkeys. Besides avian IBV the agent causing the corona viral enterites of turkeys (CET, Bluecomb disease) is described as an other avian corona virus species.

To control IB in poultry, vaccines are used on a large scale. Immunization of e.g. broiler chickens and young future layers and breeders is mainly based on live, attenuated vaccines. The live vaccine virus strains have been selected besides for their immunogenic properties on the base of their antigenic spectrum and reduced pathogenicity. Vaccines have been described containing either a particular serotype such as Connecticut (e.g. Connecticut Isolate A 5968) or Massachusetts (e.g. Baudette Type IBV 42) protecting only against the homologous type or using a vaccine derived from a particular virus strain shown to have a broader antigenic spectrum such as the H strain.

Combination of different IB serotypes in live vaccines had also been tried, however, most likely as a result of mutual interaction, protection afforded against the respective serotypes was not optimal.

It thus appeared that IB vaccines based on these frequently used IB virus strains, or combinations thereof, do not result in a complete immunization against outbursts of IB.

Novel IB vaccines according to the invention are, however, surprisingly more effective against infectious bronchitis.

These novel vaccines are characterized in that they are derived from infectious bronchitis viruses which spontaneously hemagglutinate chicken erythrocytes.

IB viruses possessing the property of spontaneously hemagglutinating chicken erythrocytes were found to occur among various IBV serotypes, e.g. of the Massachusetts type and the Connecticut but also viruses belonging to new serotypes were identified.

The immunizing potency of the virus strains showing spontaneous hemagglutination of chicken erythrocytes exceeds that of viruses belonging to the same respective serotypes but which do not spontaneously agglutinate erythrocytes.

It has also been found that IB vaccines derived from combinations of IB viruses which spontaneously agglutinate chicken erythrocytes do offer better protection than vaccines based on combinations of IBV strains from different serotypes which do not cause agglutination of chicken erythrocytes.

IB vaccines according to the invention also showed excellent immunizing properties when combined with vaccines derived from one or more non-hemagglutinating IB viruses, as well as when combined with vaccines derived from other viral isolates like vaccines against Marek's disease, New Castle disease or egg drop disease.

Novel IB vaccines according to the invention can for example be derived from the novel IB virus strains, which possess the property of spontaneously hemagglutinating chicken erythrocytes, which are deposited at the Central Veterinary Laboratory, New Haw at Weybridge, U.K., registered under the numbers VLO 10110/AVI/3; VLO 10110/AVI/4; VLO 10110/AVI/5; VLO 10110/AVI/6 and VLO 10110/AVI/7, and which correspond to the strains indicated by the internal notations D 274, D 1466, D 580, 246 G and 249 G, respectively.

The novel IBV strains were shown to belong to various serotypes. Strains 246 G and D 580 are of Massachusetts and Connecticut type, respectively. Strains D 274, 249 G and D 1466 belong to new, hitherto unreported serotypes. In table 1 are summarized the results of virus neutralisation tests (VN) in eggs, using the constant serum, diluted virus method, which show that the novel isolates D 274 and D 1466 do neither belong to the Massachusetts serotype, represented in these experiments by the Dutch vaccine strain $H_{52}$, nor to one of those North American IB serotypes not covered by the H strain vaccines. The hemagglutinating strain D 274 can be classified into the new serotype D 207 and the hemagglutinating virus D 1466 belongs to the type D 212. Strain 249 G is of the same serotype as strain D 274. This is shown in (table 2) from cross neutralization experiments (using the plaque reduction test in chicken embryo fibroblast (CEF) cells) between new isolates and specific antisera prepared in specific pathogen free (SPF) chickens.

The relevance of vaccination against the new serotype IBV strains D 274, 249 G and D 1466 is illustrated by the high incidence of these serotypes in chicken field isolates. In table 3 are given the relative numbers of flocks with antibodies against the new serotype IB viruses (3A) and the frequency with which IB viruses of the respective serotypes were isolated from flocks (3b).

The novel viruses are characterized by the following properties which enable them to be identified as avian corona viruses:

1. They possess the nucleic acid of the type RNA; virus replication in chicken embryo kidney cell (CEK) cultures was not significantly influenced by the addition of 5-fluorodesoxy-uridine to the culture medium.

2. The viruses are sensitive for lipid solvents; treatment of infectious amnion-allantoic fluid (AAF) obtained by propagating the viruses in SPF embryonated eggs with chloroform resulted in a significant reduction of the infectivity titer. This is typical for enveloped viruses containing essential lipids which is also a characteristic of avian corona viruses.

3. Examination with the electron microscope of virus preparations prepared by concentrating infected AAF in an ultra centrifuge showed virus particles of *size and shape characteristic for corona viruses* and with typical *protrusions* (15-20 nm in length) at the surface. Diameter of the particles without protrusions was 75-120 nm.

4. Using a geldiffusion test it was demonstrated that the viruses contain *antigen in common with known avian corona viruses* e.g. IBV reference strain Baudette. No antigens in common with other avian viruses could be detected, however. Specific antisera prepared against the novel strains in SPF chickens did not react with antigens prepared from avian viruses other than avian corona virus.

5. The novel virus strains *multiply in the cytoplasm* of infected cells. Suitable in vitro systems are:
embryonated SPF eggs (preferably infected by the allantoic route;
tracheal organ culture;
chicken cells and
chicken embryonic cells (preferably CEK cells).

The above data sufficiently identify these novel viruses to belong to the avian corona viruses and to be distinct from other avian viruses, e.g. avian influenza viruses, New Castle disease virus (NDV), REV virus, adeno virus, leucosis virus, reticuloendotheleosis virus, avian encephalomyelitis virus, herpes viruses including infectious laryngotraceitis virus, Marek's disease virus, pigeon and turkey herpes viruses, and infectious bursal disease virus.

The present invention also relates to the preparation of vaccines comprising avian corona viruses which display spontaneous hemagglutination as described above.

The virus can be grown in embryonated SPF chicken eggs or on a cell culture, preferably from avian tissues.

If live attenuated vaccine has to be produced, attenuation can be performed by adaptation of the virus isolates to embryonated eggs or a cell culture (preferably CEK cells) and passaging the virus in those cultures e.g. 10–200 times. An alternative approach for the production of a safe live vaccine is to select and culture suitable clones of an avian corona virus, provided they still have the property of spontaneous agglutination.

To prepare an inactivated vaccine from the novel viruses the AAF or tissue culture fluid may be inactivated by e.g. formaldehyde or β-propiolactone.

After inactivation and, if necessary, adjusting of pH and neutralizing of the inactivating agent the inactivated antigen may be mixed with an adjuvant. The adjuvant can be for example aluminium hydroxide or a composition consisting of mineral oil (e.g. Marcol ® 82, a white paraffin oil) or a vegetable oil (e.g., peanut oil) and one or more emulsifiers like Tween ® 80 and Span ® 80.

Live vaccines may be administered by eye drop, nose drop, drinking water or spray methods at an age varying from one day old to the point of lay (about 18 weeks).

Inactivated vaccines will usually be given at an age of 10–20 weeks by subcutaneous or intramuscular injection.

For live vaccines a dosage may be used in a range of log 3 to log 7 $EID_{50}$ per bird, preferably between log 4 and log 5 $EID_{50}$.

Inactivated vaccines may contain the antigenic equivalent of log 5 to log 8 $EID_{50}$ per bird dose, preferably between log 6 and log 8 $EID_{50}$.

If the vaccine (live or inactivated) contains more than one corona virus strain, each strain should be present at the dosage levels mentioned.

Combination of one or more of the novel avian corona viruses with one or more unrelated avian viruses such as e.g. NDV, Infectious Bursal Disease Virus, EDS 76 virus, Adeno or Reo viruses especially in inactivated vaccines is also part of the invention.

TABLE 1

| Virus ↓ | Serum → I 97 | I 609 | Connecticut | Florida | JMK | 3896 | 207 | 212 | H52 (Mass) | 3128 | 274 | 1466 |
|---|---|---|---|---|---|---|---|---|---|---|---|---|
| J 97 | ≧6,2 | 0,7 | 1,2 | 1,4 | 0,7 | 1,7 | 0 | 0 | 0,7 | | ≦1,5 | ≦1,9 |
| J 609 | ≦2,9 | 4,9 | ≦2,9 | ≦2,9 | ≦2,9 | 3,6 | ≦2,9 | ≦2,9 | 5,1 | | ≦2,8 | ≦2,8 |
| Connecticut | 2,1 | 2,1 | ≧6,8 | 6,1 | 1,8 | 3,6 | 1,6 | ≦1,2 | 4,1 | | ≦2,5 | ≦2,6 |
| Florida | 0,6 | 1,3 | 3,4 | ≧4,2 | 0,5 | 2,6 | 1,0 | 0 | 1,3 | | 3,0 | ≦2,3 |
| JMK | 2,8 | 1,5 | 1,4 | 2,3 | ≧6,3 | 2,8 | 1,3 | 1,0 | 1,2 | | | |
| D-3896 | ≦0,8 | 0,9 | 1,5 | 1,5 | ≦0,8 | >6,6 | 1,9 | ≦0,3 | ≦0,7 | 3,2 | | |
| D-207 | 0,5 | 0 | 0,4 | 0,5 | ≦0,3 | 2,6 | ≧5,3 | 1,3 | 1,4 | 1,4 | | |
| D-212 | 0 | 1,2 | 1,0 | 1,0 | 0,3 | 2,3 | 0,5 | 5,3 | 0,5 | 1,4 | | |
| H52 | 1,6 | 2,8 | 1,8 | 2,8 | 1,1 | 1,8 | 1,1 | 1,1 | ≧5,3 | | | |
| D-274 | 2,2 | 2,7 | 4,9 | 3,7 | 2,8 | 4,2 | 5,0 | ≦1,5 | ≦1,6 | 3,4 | ≧5,9 | 3,5 |
| D-1466 | ND | ND | ND | ND | ND | 1,8 | 1,2 | ≧4,9 | 0,5 | | | |
| D-3128 | ND | ND | ND | ND | ND | 1,5 | 0 | 0 | 0 | 6,4 | | |
| D-752 | | | | | | 1,9 | 1,5 | 1,3 | 1,5 | 1,9 | 2,0 | 3,9 |

TABLE 2

| Virus Strain ↓ | Antiserum → | | | |
|---|---|---|---|---|
| | Massachusetts | D-207 | D-212 | Connecticut |
| M41 (Mass) | ++ | − | − | − |
| D-274 | − | ++ | − | − |
| 249 G | − | ++ | − | − |
| 246 G | ++ | − | − | − |
| D-212 | − | − | ++ | − |
| D-580 | − | − | − | ++ |
| Connecticut | − | − | − | ++ |

++ = a specific antiserum diluted 1:16, causes a complete reduction of ± 40 plaques ≈
− = the same antiserum does not cause a significant reduction of the plaques count.

TABLE 3

| | Percentage of flocks with antibody against one or several new serotypes | |
|---|---|---|
| A | D 207 | D 212 |
| Serology 197 flocks monitored | 61% | 32% |

| | Number of classified isolates | | |
|---|---|---|---|
| B | Mass* | D 207 | D 212 |
| Virus isolations out of 52 flocks | 9* | 29 | 4 |

*No differentiation from H vaccine strains done.

DESCRIPTION OF THE DRAWINGS

FIG. I shows the Distribution of HI antibody titers against three (3) IB serotypes after vaccination with line D-274 vaccine. The three serotypes are, respectively HI Massachusetts, HI D-212 and D-207.

FIG. II shows a longitudinal survey of HI titers of 16 flocks vaccination at 1 day of age with H-120 at 16 weeks of age with H-52 (both Massachusetts type) and at 12 weeks of age with D-274.

··· D-207

—Massachusetts
—D-212

These figures are further discussed in Example X.
The invention is illustrated by the following examples.

EXAMPLE I

Isolation of infectious bronchitis viruses

Isolations were carried out in breeder and layer flocks using the following procedure:

Tracheal swabs and/or intestine scrapings from the caecal region were suspended in tryptose phosphate broth containing antibiotics.

At least ten 9–11 days old embryonated SPF chicken eggs were inoculated with each of the virus sample suspensions via the allantoic route.

48–72 hours p.i. allantoic fluid and CAM were harvested from four of the ten eggs inoculated for further passage in SPF eggs. At least three serial blind passages were carried out for each sample.

The remaining eggs of each passage (usually six out of ten) were incubated for seven days and the embryo still alive were examined for stunting an lesions typical for IB.

EXAMPLE II

Live vaccines

A. Preparation of the virus

Embryonated SPF chicken eggs (10–11 days incubated) are inoculated with log 3 to log 4 of the 50% egg infectious dosis ($EID_{50}$) of the seed virus in the allantoic cavity. The eggs were candled 18–24 hours p.i. and aspecific died embryos are discarded. After an incubation period of 18–72 hours (depending on the virus strain used) the AAF is harvested, clarified by centifugation and/or filtration and eventually mixed with a suitable concentration of antibiotics (when indicated).

B. Preparation of the vaccine

The AAF can subsequently be processed to a pharmaceutical preparation by methods known per se. Stabilizing can be carried out by addition of a suitable stabilizing agent such as a carbohydrate like sorbitol, mannitol or a protein like albumin, casein, or suitable mixtures. The bulk AAF can be frozen down at temperatures lower than $-35°$ C. and stored until further treatment. Alternatively the bulk is stored at $+4°$ C. until further treatment.

Samples are taken to assay the virus content. Stabilized AAF (after thawing when the material was frozen) is filled into lyophilization vials in 1–2 ml quantities. The virus content is adjusted in such a way that the titer after freezedrying is at least 4.0 log $EID_{50}$ per bird dose.

The vials are sealed under vacuum or under nitrogen after freezedrying.

EXAMPLE III

Inactivated vaccine

A. Preparation of the virus

The virus is propagated as described under IIA. Storage of the bulk prior to inactivation and further processing can be done at temperatures lower than $-35°$ C.

B. Inactivation of the virus

The frozen AAF is thawed, a sample is taken to determine the virus titer ($EID_{50}$); the AAF is inactivated by addition of formaline to a final concentration of 0.4%. After 24 hours at room temperature the formaline can be neutralized by sodium metabisulphite. A sample is tested for inactivation by inoculating in susceptible SPF chicken embryos or on CEF cultures with at least one passage. Alternative methods for inactivation are the use of $\beta$-propiolactone, ethylene-imine or derivatives thereof.

The inactivated AAF is diluted or concentrated depending on the titer requirements. Concentration can also be done prior to inactivation. Suitable methods are ultrafiltration or concentration by polyethyleneglycol precipitation.

Inactivated AAF can be stored at $+4°$ C.

C. Preparation of vaccine

To prepare an inactivated oil emulsion vaccine, Tween® 80 is added at a concentration of 3.5% to the inactivated antigen suspension. The antigenic content is adjusted to at least 7.0 $EID_{50}$ per bird dose. The antigenic mass can be determined by an enzyme immuno assay. The suspension is subsequently emulsified into the oil phase of the adjuvant in the ratio of oil to water of 70:30 or 55:45. The composition of the adjuvant is:

Marcol® 52: 90%
Tween® 80: 3.5%
Span® 80: 6.5%

The average particle size of the aqueous phase is less than 1.0 $\mu$m.

EXAMPLE IV

Combined vaccine

A. Combined live vaccine

For the preparation of a live combined vaccine AAF containing the different virus strains (prepared according to Example II) has to be combined in such a manner that the required minimal virus content for each particular strain is reached in the final product.

B. Combined inactivated vaccine

The virus strains are propagated according to Example IIA, and stored at $-35°$ C.

The antigens of the respective virus strains are inactivated according to Example IIIB and stored at $+4°$ C.

Tween®80 is added at a concentration of 3.5% to the respective antigen suspensions. The antigenic content of each particular virus suspension is adjusted such that each strain is contained in one bird dose of the vaccine with an antigenic equivalent of at least 7.0 log $EID_{50}$. The polyvalent vaccine is emulsified as described in Example IIIC; the water phase may either be mixed before emulsifying or the individual antigens may be emulsified separately prior to mixing.

EXAMPLE V

Hemagglutination of chicken erythrocytes

Two volumes of infected AAF (prepared according to Example IA) or supernatant of infected tissue cultures were mixed with 1 volume of 2% chicken erythrocyte suspension, at room temperature.

Agglutination follows within approximately 2 minutes, occasionally within 5 minutes. Hemagglutination can be accelerated by incubation at $+4°$ C.

The hemagglutinin is associated with the virus particles as can be demonstrated by bromelian treatment.

EXAMPLE VI

Hemagglutination inhibition (HI)

A. Whether the hemagglutination of chicken erythrocytes caused by the novel IB strains is specific and due to the virus antigen can be demonstrated by the inhibition of the hemagglutination reaction by the addition of specific antisera against the particular virus prior to adding the erythrocytes.

SPF eggs were inoculated with the hemagglutinating strain D 274 48 hours p.i., incubated and AAF was harvested.

The untreated AAF was used as such or diluted 1:1 with serum or antiserum. Thereafter chicken erythrocytes were added. The results are given in the table below.

TABLE 4

| Additions | HA +/− |
|---|---|
| Untreated AAF | + |
| AAF + SPF chicken serum | + |
| AAF + Specific IBV antiserum (type 207) | − |
| AAF + Specific NDV* antiserum | + |

*NDV = Newcastle Disease Virus

B. Since the novel IB viruses bear hemagglutinin (as shown by bromelian treatment) and belong to various serotypes the HI test can also be used to distinguish between the new viruses.

The method used is described by Alexander, D. J. et al. (Avian Pathology 5, 125-134 (1976)). Phospholipase C has been used to treat the respective antigens.

The titer so obtained is expressed as 2 log. The date are given in the table below.

TABLE 5

| Serum ↓ | Antigen from IBV (serotype) → | | |
|---|---|---|---|
| | M41 (Mass) | D274 (207) | D1466 (212) |
| H52 (Mass) | 9 | 6 | 5 |
| 207 | 6 | 10 | 5 |
| 212 | 5 | 5 | 8 |
| 246G (Mass) | 10 | 5 | n.d. |

EXAMPLE VII

Vaccination experiments SPF chickens

A. Propagation of viruses and preparation of vaccines

Viruses of strains D 207 (non-hemagglutinating (HA−)) and D 274 (hemagglutinating (HA+)) were cultured on SPF eggs and attenuated during 54 and 52 egg passages, respectively. Vaccines of these attenuated virus strains were prepared according to Example III.

B. Vaccination

Two groups of each 10 SPF chickens, 6 weeks of age were vaccinated by eye drop with 4.0 log $EID_{50}$ of the above respective vaccines. Hens were housed in isolators and bled for serum testing at weekly intervals. The HI titer of these sera was determined according to the method described in Example VIB, using antigen prepared from IBV D 274. The results given in the table show the development of the immunisation against D 274 antigens during 12 weeks in the two groups of vaccinated hens; a control with unvaccinated hens was included in the test.

TABLE 6

| Vaccine | Weeks after vaccination | | | | | | | | | | | | |
|---|---|---|---|---|---|---|---|---|---|---|---|---|---|
| | 0 | 1 | 2 | 3 | 4 | 6 | 7 | 8 | 9 | 10 | 11 | 12 |
| 207 (HA−) | 4.0 | 5.4 | 6.2 | 5.9 | 6.6 | 4.8 | 4.2 | 5.5 | 5.8 | 5.2 | 4.1 | 5.2 |
| 274 (HA+) | 4.7 | 7.5 | 8.2 | 8.7 | 8.2 | 10.0 | 9.3 | 10.0 | 10.1 | 9.5 | 8.8 | 9.3 |
| none | ← <5 → | | | | | | | | | | | |

In the sera of the same two groups of vaccinated hens the neutralizing response (>4.0 log) against the homologous strain D 274 ($52^e$ passage) is tested. The numbers of animals (out of ten vaccinated) showing a response are given in the table below.

TABLE 7

| Weeks after vaccination | Vaccine group | |
|---|---|---|
| | 207 (HA−) | 274 (HA+) |
| 3 | 7/10* | 9/10* |
| 12 | 5/10 | 9/10 |

C. Challenge experiments

Twelve weeks after vaccination the vaccinates and a non-vaccinated group of hatchmates were subjected to a challenge infection with 4.0 log $EID_{50}$ of strain D 274 (after 52 passages). Four days after challenge tracheal sections the birds were prepared for histological examination by immuno fluorescence (IFT) using standard techniques. The number of birds (out of ten vaccinated) showing microscopical lesions or positive IFT is listed in the table below.

TABLE 8

| Vaccine | Microscopic lesions | IFT pos. |
|---|---|---|
| 207 (HA−) | 6/10* | 2/10 |
| 274 (HA+) | 0/10 | 0/10 |
| none | 10/10 | 6/10 |

It can be concluded that a vaccine prepared from the novel hemagglutinating strain D 274 evokes high levels of HI and neutralizing antibody titers as early as one week after vaccination, persisting at a level known to be protective for at least 12 weeks p.v. This could be confirmed by a 100% protection of the D 274 group against challenge.

In contrast the non-hemagglutinating strain D 207 of the same serotype evoked only low levels of HI antibody during the experimental period. Moreover, the neutralizing antibody titer was significantly lower when compared with the hemagglutinating D 274 vaccinated group 12 weeks p.v., which is in confirmation with the significantly lower protection rate (only about 50%) in the D 207 group.

EXAMPLE VIII

Vaccination with combined live vaccine

A. Propagation of viruses and preparation of vaccines

Viruses of the hemagglutinating strains D 274 and D 1466 were propagated according to the method described in Example IA, and monovalent and polyvalent vaccines of these were prepared according to Examples IIB and IVA, respectively, with 4.0 log $EID_{50}$ of each strain.

B. Vaccination

Four groups of ten weeks old SPF chickens each were housed in four separate isolators. The hens were vaccinated by eye drop. Group A was vaccinated with strain D 274 vaccine, group B with D 1466 vaccine, group C with the combined vaccine and group D was a non vaccinated control group.

C. Testing of immunization

Blood was collected at day of vaccination and 2, 4, 6 and 8 weeks later. Sera were tested individually for homologous and heterologous HI antibody response using antigens prepared with different prototype strains (M41, D 274 and D 1466). The results are given in table 9.

TABLE 9

| Group Vaccines ↓ | Weeks after vaccination | | | | | | | | | | | | | | |
|---|---|---|---|---|---|---|---|---|---|---|---|---|---|---|---|
| | 0 | | | 2 | | | 4 | | | 6 | | | 8 | | |
| | | | | | | | Ag Type | | | | | | | | |
| | M41 | D274 | D1466 | M41 | D274 | D1466 | M41 | D274 | D1466 | M41 | D274 | D1466 | M41 | D274 | D1466 |
| (A) D 274 | 3.6 | 4.0 | 3.5 | 9.4 | 9.8 | 8.0 | 6.8 | ≧10.1 | 5.9 | 5.2 | ≧10.0 | 4.4 | 4.4 | ≧10.3 | 3.1 |
| (B) D 1466 | 3.4 | 3.7 | 3.2 | 7.0 | 5.8 | 7.3 | 5.2 | 5.1 | 7.2 | 4.1 | 4.4 | 6.8 | 4.1 | 5.1 | 6.3 |
| (C) D274 + D1466 | 3.4 | 3.9 | 3.4 | 7.8 | 8.0 | 7.3 | 6.6 | ≧9.0 | 7.3 | 5.2 | ≧8.4 | 6.4 | 5.7 | 9.0 | 6.5 |
| (D) none | 3.3 | 3.8 | 3.3 | 4.8 | 4.0 | 3.8 | ≦3.7 | ≦3.9 | 4.1 | ≦3.0 | ≦3.6 | ≦3.5 | ≦3.2 | 4.2 | ≦3.0 |

The D 274 vaccinated chickens (group A) respond with high levels of homologous HI antibodies from two weeks until the end of the experiment. At 2 and 4 weeks p.v. a significant cross reaction was observed against the heterologous antigens M41 and D 1466, disappearing between 6-8 weeks. Group B chickens showed a similar response at a lower titer level. The homologous response stays on a protective level until at least the end of the experiments (8 weeks p.v.). The combine vaccine (group C) induced long lasting high levels of HI antibodies against both vaccine strains. A marked heterologous response to the M41 antigen can also be seen at 2 and 4 weeks p.v. The early heterologous response might be explained by a higher proportion of immuno globulins reacting to the group specific antigens. It appears from this experiment that the two hemagglutinating strains D 274 and D 1466 express their immunogenic potency in both single and combined live vaccines.

EXAMPLE IX

Vaccination experiments in the field

A. Virus propagation and vaccine preparation

Live vaccines of the non hemagglutinating H 120, strains D 207 and the hemagglutinating strain D 274 viruses were prepared as described in Example VIIA.

B. Vaccination

Flocks of white leghoorn and brown hens were vaccinated at one day old with H 120 vaccine. At 10 weeks of age the white leghorn hens and the brown hens were vaccinated with vaccines of D 207 and D 274 respectively. The dose was 4.5 log EID$_{50}$ per bird. The average flock size was 15,000 birds and the vaccine was administered by spray (knapsack-sprayer).

C. Blood collection

At day of vaccination with the D 207 and D 274 vaccines 24 blood samples were taken per flock for serological investigation and this was repeated 4 weeks after vaccination.

D. Immunization control

The neutralization index (NI) was used as parameter for protection. A mean NI of more than 4 log against the respective serotype was considered to be related with effective vaccination.

TABLE 10

| Vaccine strain | Number of flocks (average size 15.000 birds) | | | |
|---|---|---|---|---|
| | Vaccinated | Pos.* at day of vaccination | Pos.* 4 weeks after vaccination | Increase of responding flocks in percentage |
| D 207 (HA−) | 10 | 4 | 6 | 40% → 60% |
| D 274 (HA+) | 20 | 4 | 18 | 20% → 90% |

*pos. = mean NI ≧ 4 log against serotype D 207.

In the table is shown that the percentage of flocks which react with a neutralizing response known to be protective is significantly higher in the D 274 group compared with the D 207 vaccine group.

EXAMPLE X

Development and distribution of HI antibody titers during vaccination experiments in the field Serological response of layer and breeder flocks after vaccination with the hemagglutinating vaccine strain D-274 has been monitored.

A total of 137 flocks with an average size of 15.000 birds were vaccinated at an age of 10-12 weeks with a single dose of live D-274 vaccine (serotype D-207) by knapsack spray administration.

Massachusetts type vaccination had been carried out in the same flocks at day old (H 120) and at about 15 weeks of age (H 52). All flocks were tested for HI antibodies against the respective serotypes Massachusetts, D-207 and D-212 at 18-20 weeks of age.

The distribution pattern of HI titers is shown in FIG. I. 16 out of the 137 flocks were followed until 38 weeks of age and HI titres measured with four weeks intervals. Results are given in FIG. II. From the 137 flocks 86% showed HI titers >7, 63% >8 and 25% >9 against the serotype D-207. The response against the Massachusetts serotype—after two vaccinations with non hemagglutinating strains—was inferior: 66% of the flocks had HI titers <7. The response against D-212 serotype (no vaccination) was as expected still lower: 82% of the flocks had a HI titer <7.

From the longitudinal survery (FIG. 2) it may also be concluded that HI titers achieved after a single vaccination with strain D-274 are consistently higher compared with those induced by two vaccinations with conventional Massachusetts vaccines.

EXAMPLE XI

Hemagglutination of chicken erythrocytes (RBC's)

The spontaneous hemagglutinating activity of the novel IBV strains as shown in the rapid plate HA test applied in the Examples V and VI was also investigated in a more quantitative way by a slow HA test in microtiter plates, in which spontaneous hemagglutination is not consistently displayed.

Since differentiation between hemagglutinating and non-hemagglutinating strains by the quantitative slow HA test in microtiter plates is desirable, we used concentrated and partly purified virus suspensions to demonstrate the HA activity.

A. Preparation of virus suspensions

Allantoic fluid harvests from 10-day-old embryonated eggs were collected 24–48 hours post-inoculation.

The AAF was clarified by centrifugation for 10 minutes at $1000 \times g$.

The virus content of 35 ml AAF was pelleted using a SW-28 rotor (Beckman) at $30.000 \times g$ for 60 minutes.

The pellet thus obtained was resuspended in 1 ml PBS (phosphate buffered saline).

B. Testing of hemagglutionation

Two-fold serial dilutions of the virus suspensions were made in microtiter plates. 25 µl RBC (1%) were added to 50 µl final volumes of virus dilutions. The plates were read after incubation for 2–18 hours at 4° C.

Titers are expressed as the reciprocal value of the highest dilution showing a more than 75% agglutination (n=number of experiments).

Results are summarized in Table 11.

TABLE 11

| Strain | HA before conc. | HA after conc. 35-fold | |
|---|---|---|---|
| | | geom. mean | range |
| AAF (neg.) | — (n = 1) | — (n = 2) | — |
| M41 | — (n = 4) | — (n = 3) | — |
| D-274 | — (n = 5) | 3 (n = 6) | 2–8 |
| 246G | — (n = 5) | 3 (n = 5) | 2–8 |
| D-1466 | — (n = 3) | 4 (n = 5) | 2–8 |

The three spontaneously hemagglutinating strains D-274, 246G and D-1466 tested here, all display HA titers between 2–8 after a 35-fold concentration step, whereas uninfected AAF (negative control) and the non-hemagglutinating reference strain M41 remained negative after the same treatment.

These experiments show that both with the slow and rapid plate HA tests hemagglutination of the novel IBV strains can be found. The concentration steps are routinely used to concentrate and partly purify IBV particles. This indicates that the HA characteristics of the described strains are associated with the virus particles.

We claim:

1. An infectious bronchitis vaccine comprising at least one infectious bronchitis virus which spontaneously hemagglutinates chicken erythrocytes.

2. An infectious bronchitis vaccine according to claim 1, wherein at least one infectious bronchitis virus is selected from the group consisting of culture numbers VLO 10110/AVI/3, VLO 10110/AVI/4, VLO 10110/AVI/5, VLO 10110/AVI/6 and VLO 10110/AVI/7 deposited at the Central Veterinary Laboratory, New Haw at Weybridge, United Kingdom.

3. A vaccine according to claim 2 in lyophilized form.

4. An infectious bronchitis vaccine according to claim 1, wherein at least one infectious bronchitis virus is a live virus present in an amount of between log 3 and log 7 $EID_{50}$ per dose of each of the viruses.

5. An infectious vaccine according to claim 1, wherein at least one infectious bronchitis virus is an inactivated virus present in an amount of between log 5 and log 8 $EID_{50}$ per dose of each of the viruses.

6. A vaccine according to claim 1 in virus suspension form.

7. A vaccine according to claim 1 in lyophilized form.

8. A process for the preparation of an infectious bronchitis vaccine according to claim 1 comprising the steps of:
   a. cultivating at least one infectious bronchitis virus which spontaneously agglutinates chicken erythrocytes,
   b. collecting cultivated virus material,
   c. followed by at least one of the following treatments of said cultivated virus material;
      i. adding acid or base to adjust the pH,
      ii. adding adjuvant,
      iii. clarifying by centrifugation and/or filtration,
      iv. adding antibiotics,
      v. adding stabilizing agent.

9. A process according to claim 8 wherein the vaccine contains a virus dose of between log 3 and log 7 $EID_{50}$ per dose of each of the viruses.

10. A vaccine according to claim 2 in virus suspension form.

11. A process for the preparation of an inactivated infectious bronchitis vaccine according to claim 1 comprising the steps of:
   a. cultivating at least one infectious bronchitis virus which spontaneously agglutinates chicken erythrocytes,
   b. collecting the cultivated virus material,
   c. inactivating the virus material,
   d. followed by at least one of the following treatments of said cultivated virus material:
      i. adding acid or base to adjust the pH,
      ii. adding adjuvant,
      iii. removing the inactivating agent, if present,
      iv. clarifying by centrifugation and/or filatration,
      v. adding antibiotics,
      vi. adding stabilizing agent.

12. A process according to claim 11 wherein the vaccine contains a virus dose of between log 5 and log 8 $EID_{50}$ per dose of each of the viruses.

13. A process according to claim 11 wherein, in step c, an inactivating agent is used.

14. A method for the immunization of poultry against infectious bronchitis which comprises administration of an immunizing amount of a vaccine according to claim 1 to said poultry.

15. A combined infectious bronchitis vaccine comprising at least one first infectious bronchitis virus which spontaneously hemagglutinates chicken erythrocytes and at least one second non-hemagglutinating infectious bronchitis virus.

16. A vaccine according to claim 15, wherein at least one first infectious bronchitis virus is selected from the group consisting of the culture numbers VLO 10110/AVI/3, VLO 10110/AVI/4, VLO 10110/AVI/5, VLO 10110/AVI/6 and VLO 10110/AVI/7 deposited at the Central Veterinary Laboratory, New Haw at Weybridge, United Kingdom.

17. A vaccine according to claim 15, wherein at least one first infectious bronchitis virus is a live virus present in an amount of between log 3 and log 7 $EID_{50}$ per dose of each of the viruses.

18. A vaccine according to claim 15, wherein at least one first infectious bronchitis virus is an inactivated virus present in an amount of between log 5 and log 8 $EID_{50}$ per dose of each of the viruses.

19. A process for the preparation of an infectious bronchitis vaccine according to claim 15 comprising subjecting each of at least one first and at least one second infectious bronchitis viruses to the following steps:
   a. cultivating the virus,
   b. collecting the cultivated virus material,
   c. followed by at least one of the following treatments of said cultivated virus material:
      i. adding acid or base to adjust the pH,
      ii. adding adjuvant,
      iii. clarifying by centrifugation and/or filtration,
      iv. adding antibiotics,
      v. adding stabilizing agent,
and mixing the live viruses following either step a, b or one of the treatments of step c.

20. A process according to claim 19, wherein each of the viruses is present in the combined vaccine in an amount of between log 3 and log 7 $EID_{50}$ per dose.

21. A process according to either claim 8 or claim 19 in which the virus is live.

22. A process for the preparation of an inactivated infectious bronchitis vaccine according to claim 15 comprising subjecting each of at least one first and at least one second infectious bronchitis viruses to the following steps:
   a. cultivating the virus,
   b. collecting the cultivated virus material,
   c. inactivating the virus material,
   d. followed by at least one of the following treatments of said cultivated virus material:
      i. adding acid or base to adjust the pH,
      ii. adding adjuvant,
      iii. removing the inactivating agent, if present,
      iv. clarifying by centrifugation and/or filtration,
      v. adding antibiotics,
      vi. adding stabilizing agent,
and mixing the viruses following either step a, b, c or one of the treatments of step d.

23. A process according to claim 22, wherein each of the viruses is present in the combined vaccine in an amount of between log 5 and log 8 $EID_{50}$ per dose.

24. A process according to claim 22 wherein, in step c, an inactivating agent is used.

25. A method for immunization of poultry against infectious bronchitis which comprises administration of an immunizing amount of a vaccine according to claim 15 to said poultry.

26. A combined vaccine comprising at least one first infectious bronchitis virus which spontaneously hemagglutinates chicken erythrocytes and at least one second virus selected from the group consisting of New Castle disease virus, infectious bursal disease virus, egg drop syndrome 76 virus, adeno virus and reo virus.

27. A combined vaccine according to claim 26, wherein at least one first infectious bronchitis virus is selected from the group consisting of culture numbers VLO 10110/AVI/3, VLO 10110/AVI/4, VLO 10110/AVI/5, VLO 10110/AVI/6 and VLO 10110/AVI/7 deposited at the Central Veterinary Laboratory, New Haw at Weybridge, United Kingdom.

28. A combined vaccine according to claim 26, wherein at least one first virus is an inactivated virus present in an amount of between log 5 and log 8 $EID_{50}$ per dose of each of the viruses.

29. A process for the preparation of an inactivated combined vaccine according to claim 26, comprising subjecting each of said viruses to the following steps:
   a. cultivating the virus,
   b. collecting the cultivated virus material,
   c. inactivating the virus material,
   d. followed by at least one of the following treatments of said cultivated virus material:
      i. adding acid or base to adjust the pH,
      ii. adding adjuvant,
      iii. removing the inactivating agent, if present,
      iv. clarifying by centrifugation and/or filtration,
      v. adding antibiotics,
      vi. adding stabilizing agent,
and mixing the viruses following either step a, b, c or one of the treatments of step d.

30. A process according to claim 29, wherein each of the infectious bronchitis viruses is present in the combined vaccine in an amount of between log 5 and log 8 $EID_{50}$ per dose.

31. A process according to claim 29 wherein, in step c, an inactivating agent is used.

32. A method for the immunization of poultry against infectious bronchitis which comprises administration of an immunizing amount of a vaccine according to claim 26 to said poultry.

33. A process according to either claim 8 or claim 19 in which the virus is attenuated.

* * * * *